(12) United States Patent
Griffin et al.

(10) Patent No.: US 8,732,209 B2
(45) Date of Patent: May 20, 2014

(54) COMPUTERIZED SYSTEM AND METHOD FOR RENDERING REPORTS IN A HEALTHCARE ENVIRONMENT

(75) Inventors: Sean Patrick Griffin, Kansas City, MO (US); Brent W. Bossi, Smithville, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 1066 days.

(21) Appl. No.: 11/145,693

(22) Filed: Jun. 6, 2005

(65) Prior Publication Data
US 2006/0150086 A1    Jul. 6, 2006

Related U.S. Application Data

(60) Provisional application No. 60/640,836, filed on Dec. 30, 2004.

(51) Int. Cl.
G06F 17/30 (2006.01)
G10L 15/22 (2006.01)
G06F 19/00 (2011.01)

(52) U.S. Cl.
CPC ................................ *G06F 19/3487* (2013.01)
USPC .......................................... 707/802; 704/250

(58) Field of Classification Search
USPC .............................................. 707/1, 101, 102
See application file for complete search history.

(56) References Cited

U.S. PATENT DOCUMENTS

| | | | |
|---|---|---|---|
| 6,250,309 B1 * | 6/2001 | Krichen et al. | 128/899 |
| 6,446,256 B1 * | 9/2002 | Hyman et al. | 717/143 |
| 6,643,652 B2 * | 11/2003 | Helgeson et al. | 707/10 |
| 6,826,578 B2 * | 11/2004 | Brackett et al. | 707/104.1 |
| 7,089,492 B2 * | 8/2006 | Anderson | 715/239 |
| 7,188,183 B1 * | 3/2007 | Paul et al. | 709/229 |
| 7,209,898 B2 * | 4/2007 | Pfeiffer et al. | 705/51 |
| 7,293,031 B1 * | 11/2007 | Dusker et al. | 707/101 |
| 7,373,422 B1 * | 5/2008 | Paul et al. | 709/238 |
| 2002/0023654 A1 * | 2/2002 | Webb | 128/899 |
| 2002/0107985 A1 * | 8/2002 | Hwang et al. | 709/246 |
| 2002/0143824 A1 * | 10/2002 | Lee et al. | 707/523 |
| 2003/0088420 A1 * | 5/2003 | alSafadi et al. | 704/270.1 |
| 2003/0103071 A1 * | 6/2003 | Lusen et al. | 345/705 |
| 2003/0194057 A1 * | 10/2003 | Dewaele | 378/210 |
| 2003/0208460 A1 * | 11/2003 | Srikant et al. | 707/1 |
| 2004/0039990 A1 * | 2/2004 | Bakar et al. | 715/505 |
| 2004/0083217 A1 * | 4/2004 | Brackett et al. | 707/100 |
| 2004/0128617 A1 * | 7/2004 | Oh | 715/513 |
| 2004/0143795 A1 * | 7/2004 | Matsuishi | 715/530 |
| 2004/0205563 A1 * | 10/2004 | Lee | 715/513 |
| 2005/0022154 A1 * | 1/2005 | Chung et al. | 717/100 |
| 2005/0066273 A1 * | 3/2005 | Zacky | 715/517 |
| 2006/0085744 A1 * | 4/2006 | Hays et al. | 715/530 |
| 2008/0201469 A1 * | 8/2008 | Reasor et al. | 709/224 |

* cited by examiner

*Primary Examiner* — Tarek Chbouki

(74) *Attorney, Agent, or Firm* — Shook Hardy & Bacon LLP

(57) ABSTRACT

Computerized systems and methods for dynamically rendering reports in a healthcare environment are provided. In accordance with one method of the invention, two XML files are provided. The first XML file contains data representing information to be presented in the report. The second XML file contains data representing a format for the report. The second XML file is converted to an XSL stylesheet and applied to the data contained in the first XML file to create a third XML file. The third XML file contains the data representing the information to be presented in the report and the data representing the format for the report. The report is rendered using the third XML file.

13 Claims, 20 Drawing Sheets

```
<?xml version="1.0" encoding="iso-8859-1" ?>
- <chart request-id="12345">
   - <demographics>
       <person-info patient-name="Sean P. Charting" sex="Male" dob="Jul 31, 1978" ssn="111-22-
       3333" />
       <encounter-info client="Baseline East Medical Center" facility="BEMC" admit-dttm="Jan 8,
       2003 11:16" />
   </demographics>
   - <clinical-data>
      - <lab-data>
         - <accession number="03-134-56" collected-dttm="Jan 9, 2003 10:00">
             <dta name="Creatinine" unit="mg/dL" result-value="001" />
             <dta name="Chloride" unit="mEq/L" result-value="102.3" />
           </accession>
         - <accession number="03-135-07" collected-dttm="Jan 10, 2003 14:30">
             <dta name="Creatinine" unit="mg/dL" result-value="005" />
             <dta name="Chloride" unit="mEq/L" result-value="102.2" />
           </accession>
         - <accession number="03-138-43" collected-dttm="Jan 13, 2003 08:14">
             <dta name="Creatinine" unit="mg/dL" result-value="007" />
             <dta name="Chloride" unit="mEq/L" result-value="100.9" />
           </accession>
       </lab-data>
   </clinical-data>
</chart>
```

```xml
<?xml version="1.0" encoding="iso-8859-1" ?>
<xsl:stylesheet version="1.0" xmlns:xsl="http://www.w3.org/1999/XSL/Transform">
  <xsl:template match="/">
    <xsl:element name="xsl:stylesheet"
        namespace="http://www.w3.org/1999/XSL/Transform">
      <xsl:attribute name="version">1.0</xsl:attribute>
      <xsl:element name="xsl:template">
        <xsl:attribute name="match">chart</xsl:attribute>
        <xsl:element name="chart">
          <xsl:attribute name="request-id">{@request-id}</xsl:attribute>
          <xsl:element name="xsl:apply-templates">
            <xsl:attribute name="select">demographics</xsl:attribute>
          </xsl:element>
          <xsl:element name="xsl:apply-templates">
            <xsl:attribute name="select">clinical-data</xsl:attribute>
          </xsl:element>
        </xsl:element>
      </xsl:element>
      <!-- ******************* HEADER *********************** -->
      <xsl:element name="xsl:template">
        <xsl:attribute name="match">demographics</xsl:attribute>
        <xsl:element name="xsl:copy">
          <xsl:element name="xsl:for-each">
            <xsl:attribute name="select">*</xsl:attribute>
            <xsl:element name="xsl:copy">
              <xsl:element name="xsl:for-each">
                <xsl:attribute name="select">@*</xsl:attribute>
                <xsl:element name="xsl:variable">
                  <xsl:attribute name="name">attrib-name</xsl:attribute>
                  <xsl:attribute name="select">name()</xsl:attribute>
                </xsl:element>
                <xsl:element name="xsl:choose">
                  <xsl:for-each select="//header/descendant::data-element">
                    <xsl:element name="xsl:when">
                      <xsl:attribute name="test">
                        $attrib-name = '
                        <xsl:value-of select="@type" />
                        '
                      </xsl:attribute>
                      <data-element literal="{@literal}">
                        <xsl:element name="xsl:value-of">
                          <xsl:attribute name="select">.</xsl:attribute>
                        </xsl:element>
                      </data-element>
                    </xsl:element>
                  </xsl:for-each>
                </xsl:element>
              </xsl:element>
            </xsl:element>
          </xsl:element>
        </xsl:element>
      </xsl:element>
```

```
<!-- ******************** BODY ************************* -->
<xsl:element name="xsl:template">
  <xsl:attribute name="match">clinical-data</xsl:attribute>
  <xsl:element name="xsl:copy">
    <xsl:for-each select="//body/clinical-data">
      <xsl:element name="xsl:apply-templates">
        <xsl:attribute name="select">
          <xsl:value-of select="@type" />
        </xsl:attribute>
        <xsl:if test="@format">
          <xsl:attribute name="mode">
            <xsl:value-of select="@format" />
          </xsl:attribute>
        </xsl:if>
        <xsl:if test="@section-name">
          <xsl:element name="xsl:with-param">
            <xsl:attribute name="name">section-name</xsl:attribute>
            <xsl:value-of select="@section-name" />
          </xsl:element>
        </xsl:if>
      </xsl:element>
    </xsl:for-each>
  </xsl:element>
</xsl:element>
<!-- **************** VERTICAL SECTION ******************** -->
<xsl:element name="xsl:template">
  <xsl:attribute name="match">lab-data</xsl:attribute>
  <xsl:attribute name="mode">vertical</xsl:attribute>
  <xsl:element name="xsl:param">
    <xsl:attribute name="name">section-name</xsl:attribute>
    [No Section Header]
  </xsl:element>
  <xsl:element name="vertical-lab-data">
    <xsl:attribute name="section-name">{$section-name}</xsl:attribute>
    <xsl:element name="xsl:variable">
      <xsl:attribute name="name">distinct-dtas</xsl:attribute>
      <xsl:attribute name="select">accession/dta[not(@name =
        preceding::accession/dta/@name)]</xsl:attribute>
    </xsl:element>
    <xsl:element name="xsl:for-each">
      <xsl:attribute name="select">accession</xsl:attribute>
      <xsl:element name="xsl:copy">
        <xsl:element name="xsl:copy-of">
          <xsl:attribute name="select">@*</xsl:attribute>
        </xsl:element>
      </xsl:element>
    </xsl:element>
    <xsl:element name="xsl:for-each">
      <xsl:attribute name="select">$distinct-dtas</xsl:attribute>
      <xsl:element name="xsl:variable">
        <xsl:attribute name="name">dta-name</xsl:attribute>
        <xsl:attribute name="select">self::dta/@name</xsl:attribute>
```

FIG. 7B.

```
            </xsl:element>
          - <xsl:element name="xsl:variable">
              <xsl:attribute name="name">set-of-result-vals</xsl:attribute>
              <xsl:attribute name="select">../../accession/dta[@name = $dta-
                  name]/@result-value</xsl:attribute>
            </xsl:element>
          - <xsl:element name="xsl:copy">
            - <xsl:element name="xsl:copy-of">
                <xsl:attribute name="select">@name | @unit</xsl:attribute>
              </xsl:element>
            - <xsl:element name="xsl:for-each">
                <xsl:attribute name="select">$set-of-result-vals</xsl:attribute>
              - <result>
                - <xsl:element name="xsl:choose">
                  - <xsl:element name="xsl:when">
                      <xsl:attribute name="test">string(.)</xsl:attribute>
                    - <xsl:element name="xsl:value-of">
                        <xsl:attribute name="select">.</xsl:attribute>
                      </xsl:element>
                    </xsl:element>
                    <xsl:element name="xsl:otherwise">-</xsl:element>
                  </xsl:element>
                </result>
              </xsl:element>
            </xsl:element>
          </xsl:element>
        </xsl:element>
      </xsl:element>
    </xsl:element>
  </xsl:template>
</xsl:stylesheet>
```

FIG. 7C.

```xml
<?xml version="1.0" encoding="utf-8" ?>
<xsl:stylesheet xmlns:xsl="http://www.w3.org/1999/XSL/Transform" version="1.0">
  <xsl:template match="chart">
    <chart request-id="{@request-id}">
      <xsl:apply-templates select="demographics" />
      <xsl:apply-templates select="clinical-data" />
    </chart>
  </xsl:template>
  <xsl:template match="demographics">
    <xsl:copy>
      <xsl:for-each select="*">
        <xsl:copy>
          <xsl:for-each select="@*">
            <xsl:variable name="attrib-name" select="name()" />
            <xsl:choose>
              <xsl:when test="$attrib-name = 'patient-name'">
                <data-element literal="Patient Name">
                  <xsl:value-of select="." />
                </data-element>
              </xsl:when>
              <xsl:when test="$attrib-name = 'ssn'">
                <data-element literal="Social Security #">
                  <xsl:value-of select="." />
                </data-element>
              </xsl:when>
              <xsl:when test="$attrib-name = 'client'">
                <data-element literal="Client">
                  <xsl:value-of select="." />
                </data-element>
              </xsl:when>
              <xsl:when test="$attrib-name = 'admit-dttm'">
                <data-element literal="Admit Dt/Tm">
                  <xsl:value-of select="." />
                </data-element>
              </xsl:when>
            </xsl:choose>
          </xsl:for-each>
        </xsl:copy>
      </xsl:for-each>
    </xsl:copy>
  </xsl:template>
  <xsl:template match="clinical-data">
    <xsl:copy>
      <xsl:apply-templates select="lab-data" mode="vertical">
        <xsl:with-param name="section-name">Vertical Lab</xsl:with-param>
      </xsl:apply-templates>
    </xsl:copy>
  </xsl:template>
  <xsl:template match="lab-data" mode="vertical">
    <xsl:param name="section-name">[No Section Header]</xsl:param>
    <vertical-lab-data section-name="{$section-name}">
      <xsl:variable name="distinct-dtas" select="accession/dta[not(@name =
```

```
preceding::accession/dta/@name)]" />
- <xsl:for-each select="accession">
  - <xsl:copy>
      <xsl:copy-of select="@*" />
    </xsl:copy>
  </xsl:for-each>
- <xsl:for-each select="$distinct-dtas">
    <xsl:variable name="dta-name" select="self::dta/@name" />
    <xsl:variable name="set-of-result-vals" select="../../accession/dta[@name = $dta-
       name]/@result-value" />
  - <xsl:copy>
      <xsl:copy-of select="@name | @unit" />
    - <xsl:for-each select="$set-of-result-vals">
      - <result>
        - <xsl:choose>
          - <xsl:when test="string(.)">
              <xsl:value-of select="." />
            </xsl:when>
            <xsl:otherwise>-</xsl:otherwise>
          </xsl:choose>
        </result>
      </xsl:for-each>
    </xsl:copy>
  </xsl:for-each>
</vertical-lab-data>
</xsl:template>
</xsl:stylesheet>
```

FIG. 8B.

```xml
<?xml version="1.0" encoding="utf-8" ?>
<chart request-id="12345">
  <demographics>
    <person-info>
      <data-element literal="Patient Name">Sean P. Charting</data-element>
      <data-element literal="Social Security #">111-22-3333</data-element>
    </person-info>
    <encounter-info>
      <data-element literal="Client">Baseline East Medical Center</data-element>
      <data-element literal="Admit Dt/Tm">Jan 8, 2003 11:16</data-element>
    </encounter-info>
  </demographics>
  <clinical-data>
    <vertical-lab-data section-name="Vertical Lab">
      <accession number="03-134-56" collected-dttm="Jan 9, 2003 10:00" />
      <accession number="03-135-07" collected-dttm="Jan 10, 2003 14:30" />
      <accession number="03-138-43" collected-dttm="Jan 13, 2003 08:14" />
      <dta name="Creatinine" unit="mg/dL">
        <result>001</result>
        <result>005</result>
        <result>007</result>
      </dta>
      <dta name="Chloride" unit="mEq/L">
        <result>102.3</result>
        <result>102.2</result>
        <result>100.9</result>
      </dta>
    </vertical-lab-data>
  </clinical-data>
</chart>
```

```xml
<?xml version="1.0" encoding="iso-8859-1" ?>
<xsl:stylesheet version="1.0" xmlns:xsl="http://www.w3.org/1999/XSL/Transform"
    xmlns:fo="http://www.w3.org/1999/XSL/Format">
    <xsl:include href="sect_vertical_lab.xsl" />
    <xsl:template match="chart">
        <fo:root xmlns:fo="http://www.w3.org/1999/XSL/Format">
            <fo:layout-master-set>
                <fo:simple-page-master master-name="all-pages" margin="0.5in" page-width="8.5in"
                    page-height="11in">
                    <fo:region-before extent="1in" />
                    <fo:region-after extent="0.5in" />
                    <fo:region-body margin-top="1in" margin-bottom="0.5in" />
                </fo:simple-page-master>
            </fo:layout-master-set>
            <fo:page-sequence master-reference="all-pages">
                <fo:static-content flow-name="xsl-region-before">
                    <xsl:apply-templates select="demographics" />
                </fo:static-content>
                <fo:static-content flow-name="xsl-region-after">
                    <fo:block border-top="0.3mm solid black" text-align="end" padding-top="1mm"
                        padding-bottom="1mm">
                        Page
                        <fo:page-number />
                    </fo:block>
                </fo:static-content>
                <fo:flow flow-name="xsl-region-body">
                    <xsl:apply-templates select="clinical-data" />
                </fo:flow>
            </fo:page-sequence>
        </fo:root>
    </xsl:template>
    <xsl:template match="demographics">
        <fo:table table-layout="fixed" width="100%" border-bottom="0.3mm solid black" padding-top="1mm" padding-bottom="1mm">
            <fo:table-column column-width="proportional-column-width(2)" number-columns-repeated="2" />
            <fo:table-body>
                <fo:table-row>
                    <fo:table-cell>
                        <fo:list-block provisional-distance-between-starts="1.5in" provisional-label-separation="0.15in">
                            <xsl:apply-templates select="person-info" />
                        </fo:list-block>
                    </fo:table-cell>
                    <fo:table-cell>
                        <fo:list-block provisional-distance-between-starts="1.5in" provisional-label-separation="0.15in">
                            <xsl:apply-templates select="encounter-info" />
                        </fo:list-block>
                    </fo:table-cell>
                </fo:table-row>
            </fo:table-body>
```

```
          </fo:table>
       </xsl:template>
   - <xsl:template match="person-info | encounter-info">
       - <xsl:for-each select="data-element">
          - <fo:list-item>
             - <fo:list-item-label end-indent="label-end()">
                - <fo:block text-align="start">
                     <xsl:value-of select="@literal" />
                     :
                  </fo:block>
               </fo:list-item-label>
             - <fo:list-item-body start-indent="body-start()">
                - <fo:block text-align="start">
                     <xsl:value-of select="." />
                  </fo:block>
               </fo:list-item-body>
          </fo:list-item>
       </xsl:for-each>
    </xsl:template>
</xsl:stylesheet>
```

FIG. 10B.

```xml
<?xml version="1.0" encoding="iso-8859-1" ?>
<xsl:stylesheet version="1.0" xmlns:xsl="http://www.w3.org/1999/XSL/Transform"
  xmlns:fo="http://www.w3.org/1999/XSL/Format">
  <xsl:template match="vertical-lab-data">
    <fo:block space-after="2em">
      <fo:table table-layout="fixed" width="100%">
        <fo:table-column column-width="proportional-column-width(1)" />
        <fo:table-header>
          <fo:table-row>
            <fo:table-cell>
              <!-- SECTION HEADER -->
              <fo:block background-color="#cccccc" border="0.3mm solid #999999"
                space-after="1em" text-align="center" font-style="italic" padding-
                top="2px">
                <xsl:value-of select="@section-name" />
              </fo:block>
            </fo:table-cell>
          </fo:table-row>
        </fo:table-header>
        <fo:table-body>
          <fo:table-row>
            <fo:table-cell>
              <!-- FLOWSHEET TABLE -->
              <fo:table table-layout="fixed" width="100%" border-collapse="collapse">
                <xsl:variable name="num-columns" select="count(./accession)+1" />
                <xsl:variable name="num-rows" select="count(./dta)+1" />
                <fo:table-column column-width="proportional-column-width({$num-
                  columns})" number-columns-repeated="({$num-columns})" />
                <fo:table-header>
                  <fo:table-row>
                    <fo:table-cell>
                      <fo:block text-align="end" />
                    </fo:table-cell>
                    <xsl:for-each select="./accession">
                      <fo:table-cell border="0.2mm solid #dddddd" background-
                        color="#eeeeee">
                        <fo:block text-align="center">
                          <xsl:value-of select="@collected-dttm" />
                        </fo:block>
                      </fo:table-cell>
                    </xsl:for-each>
                  </fo:table-row>
                </fo:table-header>
                <fo:table-body>
                  <xsl:for-each select="./dta">
                    <fo:table-row border-left-width="0.2mm" border-left-style="solid"
                      border-left-color="#dddddd">
                      <fo:table-cell border="0.2mm solid #dddddd">
                        <fo:block>
                          <xsl:value-of select="@name" />
                        </fo:block>
                      </fo:table-cell>
```

```
- <xsl:for-each select="result">
    - <fo:table-cell border="0.2mm solid #dddddd">
       - <fo:block text-align="center">
            <xsl:value-of select="." />
         </fo:block>
       </fo:table-cell>
    </xsl:for-each>
   </fo:table-row>
  </xsl:for-each>
 </fo:table-body>
</fo:table>
        </fo:table-cell>
       </fo:table-row>
     </fo:table-body>
    </fo:table>
   </fo:block>
  </xsl:template>
</xsl:stylesheet>
```

FIG. 11B.

```xml
<?xml version="1.0" encoding="utf-8"?>
<fo:root xmlns:fo="http://www.w3.org/1999/XSL/Format">
  <fo:layout-master-set>
    <fo:simple-page-master master-name="all-pages" margin="0.5in"
page-width="8.5in" page-height="11in">
      <fo:region-before extent="1in"/>
      <fo:region-after extent="0.5in"/>
      <fo:region-body margin-top="1in" margin-bottom="0.5in"/>
    </fo:simple-page-master>
  </fo:layout-master-set>
  <fo:page-sequence master-reference="all-pages">
    <fo:static-content flow-name="xsl-region-before">
      <fo:table table-layout="fixed" width="100%" border-bottom="0.3mm solid
black" padding-top="1mm" padding-bottom="1mm">
        <fo:table-column column-width="proportional-column-width(2)"
number-columns-repeated="2"/>
        <fo:table-body>
          <fo:table-row>
            <fo:table-cell>
              <fo:list-block provisional-distance-between-starts="1.5in"
provisional-label-separation="0.15in">
                <fo:list-item>
                  <fo:list-item-label end-indent="label-end()">
                    <fo:block text-align="start">Patient Name:</fo:block>
                  </fo:list-item-label>
                  <fo:list-item-body start-indent="body-start()">
                    <fo:block text-align="start">Sean P. Charting</fo:block>
                  </fo:list-item-body>
                </fo:list-item>
                <fo:list-item>
                  <fo:list-item-label end-indent="label-end()">
                    <fo:block text-align="start">Social Security #:</fo:block>
                  </fo:list-item-label>
                  <fo:list-item-body start-indent="body-start()">
                    <fo:block text-align="start">111-22-3333</fo:block>
                  </fo:list-item-body>
                </fo:list-item>
              </fo:list-block>
            </fo:table-cell>
            <fo:table-cell>
              <fo:list-block provisional-distance-between-starts="1.5in"
provisional-label-separation="0.15in">
                <fo:list-item>
                  <fo:list-item-label end-indent="label-end()">
                    <fo:block text-align="start">Client:</fo:block>
                  </fo:list-item-label>
                  <fo:list-item-body start-indent="body-start()">
                    <fo:block text-align="start">Baseline East Medical
Center</fo:block>
                  </fo:list-item-body>
                </fo:list-item>
                <fo:list-item>
                  <fo:list-item-label end-indent="label-end()">
                    <fo:block text-align="start">Admit Dt/Tm:</fo:block>
                  </fo:list-item-label>
                  <fo:list-item-body start-indent="body-start()">
                    <fo:block text-align="start">Jan 8, 2003 11:16</fo:block>
                  </fo:list-item-body>
                </fo:list-item>
              </fo:list-block>
            </fo:table-cell>
          </fo:table-row>
        </fo:table-body>
      </fo:table>
    </fo:static-content>
    <fo:static-content flow-name="xsl-region-after">
      <fo:block border-top="0.3mm solid black" text-align="end" padding-top="1mm"
padding-bottom="1mm">
```

```
      Page <fo:page-number/>
    </fo:block>
  </fo:static-content>
  <fo:flow flow-name="xsl-region-body">
    <fo:block space-after="2em">
      <fo:table table-layout="fixed" width="100%">
        <fo:table-column column-width="proportional-column-width(1)"/>
        <fo:table-header>
          <fo:table-row>
            <fo:table-cell>
              <fo:block background-color="#cccccc" border="0.3mm solid #999999"
space-after="1em" text-align="center" font-style="italic"
padding-top="2px">Vertical Lab</fo:block>
            </fo:table-cell>
          </fo:table-row>
        </fo:table-header>
        <fo:table-body>
          <fo:table-row>
            <fo:table-cell>
              <fo:table table-layout="fixed" width="100%"
border-collapse="collapse">
                <fo:table-column column-width="proportional-column-width(4)"
number-columns-repeated="(4)"/>
                <fo:table-header>
                  <fo:table-row>
                    <fo:table-cell>
                      <fo:block text-align="end"/>
                    </fo:table-cell>
                    <fo:table-cell border="0.2mm solid #dddddd"
background-color="#eeeeee">
                      <fo:block text-align="center">Jan 9, 2003
10:00</fo:block>
                    </fo:table-cell>
                    <fo:table-cell border="0.2mm solid #dddddd"
background-color="#eeeeee">
                      <fo:block text-align="center">Jan 10, 2003
14:30</fo:block>
                    </fo:table-cell>
                    <fo:table-cell border="0.2mm solid #dddddd"
background-color="#eeeeee">
                      <fo:block text-align="center">Jan 13, 2003
08:14</fo:block>
                    </fo:table-cell>
                  </fo:table-row>
                </fo:table-header>
                <fo:table-body>
                  <fo:table-row border-left-width="0.2mm"
border-left-style="solid" border-left-color="#dddddd">
                    <fo:table-cell border="0.2mm solid #dddddd">
                      <fo:block>Creatinine</fo:block>
                    </fo:table-cell>
                    <fo:table-cell border="0.2mm solid #dddddd">
                      <fo:block text-align="center">001</fo:block>
                    </fo:table-cell>
                    <fo:table-cell border="0.2mm solid #dddddd">
                      <fo:block text-align="center">005</fo:block>
                    </fo:table-cell>
                    <fo:table-cell border="0.2mm solid #dddddd">
                      <fo:block text-align="center">007</fo:block>
                    </fo:table-cell>
                  </fo:table-row>
                  <fo:table-row border-left-width="0.2mm"
border-left-style="solid" border-left-color="#dddddd">
                    <fo:table-cell border="0.2mm solid #dddddd">
                      <fo:block>Chloride</fo:block>
                    </fo:table-cell>
                    <fo:table-cell border="0.2mm solid #dddddd">
                      <fo:block text-align="center">102.3</fo:block>
```

FIG. 12B.

```
          </fo:table-cell>
          <fo:table-cell border="0.2mm solid #dddddd">
            <fo:block text-align="center">102.2</fo:block>
          </fo:table-cell>
          <fo:table-cell border="0.2mm solid #dddddd">
            <fo:block text-align="center">100.9</fo:block>
          </fo:table-cell>
        </fo:table-row>
      </fo:table-body>
    </fo:table>
        </fo:table-cell>
      </fo:table-row>
    </fo:table-body>
  </fo:table>
    </fo:block>
  </fo:flow>
  </fo:page-sequence>
</fo:root>
```

| Patient Name: | Sean P. Charting | Client: | Baseline East Medical Center |
| --- | --- | --- | --- |
| Social Security #: | 111-22-3333 | Admit Dt/Tm: | Jan 8, 2003 11:16 |

| Vertical Lab | | | |
| --- | --- | --- | --- |
|  | Jan 9, 2003 10:00 | Jan 10, 2003 14:30 | Jan 13, 2003 08:14 |
| Creatinine | 001 | 005 | 007 |
| Chloride | 102.3 | 102.2 | 100.9 |

Page 1

FIG. 13.

COMPUTERIZED SYSTEM AND METHOD FOR RENDERING REPORTS IN A HEALTHCARE ENVIRONMENT

CROSS-REFERENCE TO RELATED APPLICATIONS

This application claims the benefit of U.S. Provisional Application No. 60/640,836, filed Dec. 30, 2004.

STATEMENT REGARDING FEDERALLY SPONSORED RESEARCH OR DEVELOPMENT

Not applicable.

TECHNICAL FIELD

The present invention relates to the field of computer software. More specifically, some embodiments of the present invention relate to systems and methods for rendering reports using Extensible Mark-up Language and Extensible Stylesheet Language.

BACKGROUND

Many markets, such as healthcare, financial, business administration, and governmental markets, must produce publish-quality reports from predefined templates to meet client, regulatory, and other needs. Often, the markets require mass generation of reports with varying formats, requiring the use of numerous predefined templates. One solution for rendering such reports utilizes a fixed format approach. For example, a core architecture may be centered on a word processing software, in which the format for each report is represented as a template for the word processing software. Data for each report is retrieved and inserted into the template for the report using macros. However, this architecture lacks scalability, flexibility, and requires significant maintenance costs to maintain the various templates. For example, templates for different reports may contain certain common sections. When the format of each common section is built or changed, the work must be repeated for each template.

The healthcare industry is one area in particular that requires extensive record reporting and illustrates some limitations to current fixed format approaches to rendering reports. Regulations often place strict documentation requirements on healthcare facilities, such as hospitals and physician clinics. In addition, in order to provide proper care, it is essential that medical providers, such as physicians and nurses, have access to clinical charts with accurate medical information regarding patients they treat. One limitation of a current fixed format approach to rendering reports is that the templates used are often updated and previous versions of the templates are not maintained. If a clinical chart was previously created using a template that has since been updated or replaced, it may be difficult and possibly even impossible to recreate the clinical chart. The current template may produce a clinical chart that is unintelligible or incorrect as the data and template no longer correspond. For instance, the data pulled may not be located properly in the template, producing an inaccurate or incomprehensible chart.

Another limitation of some current fixed format approaches to rendering reports, such as the one described above, is that when templates are modified, the servers maintaining the templates must be taken out of service. As a result, the ability to produce clinical charts and provide medical providers access to patients' medical information is disrupted during the time the templates are being modified.

As can be seen, there are numerous limitations to the current fixed format approach described above. An alternative approach would be to utilize an architecture based on Extensible Mark-up Language (XML) and Extensible Stylesheet Language (XSL), in which an XSL stylesheet is written by a user and used to define the format for each report. An XML document is simply a document that uses mark-up tags to describe the data within the document. XML is human readable and can be easily modified with any standard text editor. XSL is a powerful language for transforming an XML document into another document. A formatted report could be produced by using a user-written XSL stylesheet, which contains formatting information, to transform an XML document, which contains report data. However, under this approach, a separate XSL stylesheet would have to be written for each report template. Because XSL is not generally human readable, this approach would require the user to be XSL savvy from the standpoint of writing the stylesheet, as well as reviewing and debugging the stylesheet. In addition, because XSL is dependent on the context of the surrounding code, storing different sections of the XSL file as separate XSL files that may be shared across multiple templates is not feasible.

Accordingly, a system for rendering reports, wherein the template for each report may be dynamically created from selected input parameters would be desirable. Further, it would be advantageous if the system permitted template modification while maintaining the ability to accurately render reports. In addition, a system in which sections may be shared among templates would also be advantageous. It would be further beneficial if the system employed a language that is human readable, making it conducive to reviewing and debugging.

SUMMARY OF THE INVENTION

Embodiments of the present invention relate to computerized systems and methods in a healthcare environment for dynamically rendering reports using Extensible Markup Language (XML) and Extensible Stylesheet Language (XSL). In one aspect, an embodiment of the present invention relates to a computerized method in a healthcare environment for dynamically rendering a report. The method includes providing two XML input files, the first XML file containing data representing information to be presented in the report and the second XML file containing data representing a format for the report. The method further includes converting the second XML file to an XSL stylesheet and applying the XSL stylesheet to the data contained in the first XML file to create a third XML file. The third XML file contains the data representing the information to be presented in the report and the data representing the format for the report. Still further, the method includes rendering the report using the third XML file.

In another aspect, an embodiment of the present invention relates to a computerized system for dynamically rendering a report in a healthcare environment. The system includes a providing component, an XSL processing component, and a report rendering component. The providing component is capable of providing a first XML file and a second XML file, the first XML file containing data representing information to be presented in the report and the second XML file containing data representing a format for the report. The XSL processing component is capable of converting the second XML file to an XSL stylesheet and applying the XSL stylesheet to the data contained in the first XML file to create a third XML file. The third XML file contains the data representing the information to be presented in the report and the data representing the format for the report. The report rendering component is capable of rendering the report using the third XML file.

BRIEF DESCRIPTION OF THE DRAWINGS

The present invention is described below in detail with reference to the attached drawing figures, wherein:

FIG. 5 is an exemplary XML file containing report data in accordance with an embodiment of the present invention;

FIG. 7A-7C are an exemplary template converter stylesheet file in accordance with an embodiment of the present invention;

FIG. 8A-8B are an exemplary XSL report template file in accordance with an embodiment of the present invention;

FIG. 9 is an exemplary XML formatted report file in accordance with an embodiment of the present invention;

FIG. 10A-10B are an exemplary report renderer file in accordance with an embodiment of the present invention;

FIG. 11A-11B are an exemplary report renderer reference file in accordance with an embodiment of the present invention;

FIG. 12A-12C are an exemplary XSL-FO formatted report file in accordance with an embodiment of the present invention; and FIG. 13 is an exemplary PDF report rendered using the files of FIG. 5 though FIG. 12 in accordance with an embodiment of the present invention.

DETAILED DESCRIPTION OF THE INVENTION

Figure 1:
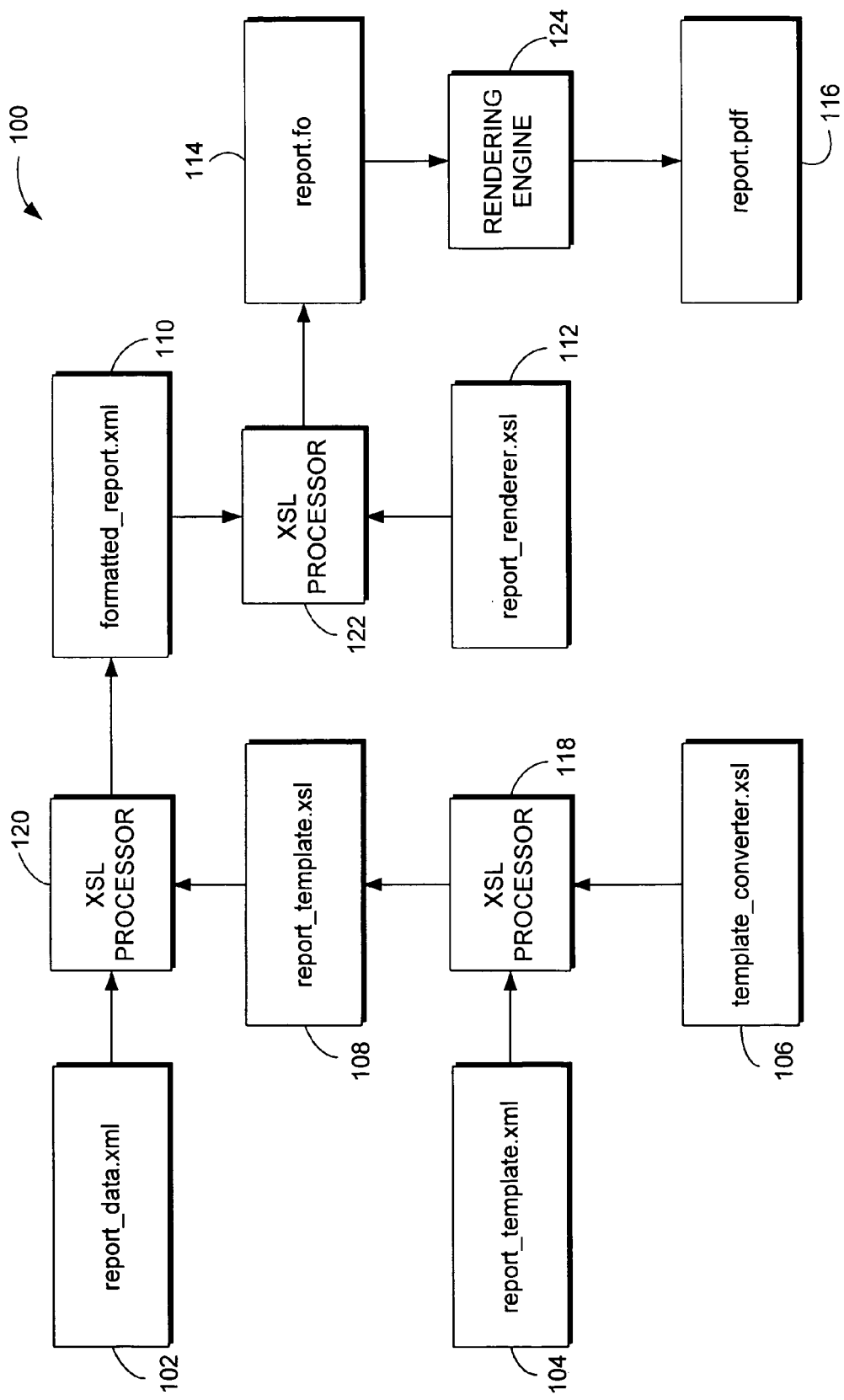
FIG. 1 is a block diagram of a system for rendering reports in accordance with an embodiment of the present invention.

The present invention may be implemented in a variety of computing system environments. For example, the invention may be embodied in an application program running on one or more personal computers (PCs). This computing system environment is only one example of a suitable computing environment and is not intended to suggest any limitation as to the scope of use or functionality of the invention. The invention may also be implemented with numerous other general purpose or special purpose computing system environments or configurations. Examples of other well-known computing systems, environments, and/or configurations that may be suitable for use with the invention include, but are not limited to, server computers, hand-held or laptop devices, multiprocessor systems, microprocessor-based systems, programmable consumer electronics, network PCs, minicomputers, mainframe computers, distributed computing environments that include any of the above systems or devices, and the like.

The invention may be described in the general context of computer-executable instructions, such as program modules. Generally, program modules include routines, programs, objects, components, segments, schemas, data structures, etc. that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Computers typically include a variety of computer-readable media. Computer-readable media includes any media that can be accessed by a computer and includes both volatile and nonvolatile media, removable and non-removable media. By way of example, and not limitation, computer-readable media may comprise computer storage media and communications media. Computer storage media include both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD), holographic or other optical storage, magnetic cassettes, magnetic tape, magnetic disk storage or other magnetic storage devices, or any other medium which can be used to store the desired information and which can be accessed by a computer.

Communications media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communications media includes wired media such as a wired network or direct wired connection, and wireless media such as acoustic, RF, infrared, spread spectrum and other wireless media. Communications media are commonly used to upload and download information in a network environment, such as the Internet. Combinations of any of the above should also be included within the scope of computer-readable media.

The computer may operate in a networked environment using logical connections to one or more remote computers, such as a personal computer, a server, a router, a network PC, a peer device or other common network node, and typically includes many or all of the elements described above. The logical connections may include connections to a local area network (LAN), a wide area network (WAN) and/or other networks. Such networking environments are commonplace in offices, enterprise-wide computer networks, intranets and the Internet.

Computer storage mechanisms and associated media provide storage of computer-readable instructions, data structures, program modules and other data for the computer. A user may enter commands and information into the computer through input devices such as a keyboard and pointing device, commonly referred to as a mouse, trackball or touch pad. Other input devices may include a microphone, touchscreen, camera, joystick, game pad, scanner, or the like. In addition to a monitor or other type of display device, computers may also include other peripheral output devices such as speakers and printers, which may be connected through an output peripheral interface.

Although many other internal components of computers have not been discussed herein, those of ordinary skill in the art will appreciate that such components and their interconnection are well-known. Accordingly, additional details concerning the internal construction of computers need not be disclosed in connection with the present invention.

Embodiments of the present invention provide systems and methods for dynamically rendering reports using Extensible Markup Language (XML) and Extensible Stylesheet Language (XSL). With reference to FIG. 1, a block diagram of an exemplary embodiment of the present invention is provided that illustrates a system for rendering reports 100. The system 100 employs a number of files to render a formatted report, including: (1) two input files, report_data.xml 102 and report_template.xml 104; (2) three stylesheets, template_converter.xsl 106, report_template.xsl 108, and report_renderer.xsl 112; and (3) two intermediate files, formatted_report.xml 110 and report.fo 114. One skilled in the art will recognize that each file 102, 104, 106, 108, 110, 112, 114 may be comprised of multiples files within the scope of the present invention.

The rendering process depicted in FIG. 1 uses two input files, report_data.xml 102 and report_template.xml 104, to render a report. The first input file, report_data.xml 102, is an XML representation of the report data. It is an XML file that contains the raw data to be presented in the report. The file 102 generally does not contain any information regarding how the data should be formatted and presented.

The second input file, report_template.xml 104, is an XML representation of the selected parameters for the template for the report. The file 104 may contain a number of components. By way of example only and not limitation, the file 104 may contain global template parameters, such as page size and where to place footnotes. The file 104 may also contain header and footer parameters, such as which data elements should be used to populate the header and footer and where the data elements should be placed in the header and footer. In addition, the file 104 may contain selected parameters for each section associated with the template, such as which data elements should be presented and how the data should be displayed. In an embodiment, the various components of the file 104 may be stored as separate XML files, which may be used as building blocks to construct report_template.xml 104 as a single file.

The system 100 also employs several stylesheets that are used for transforming the XML files. The first stylesheet, template_converter.xsl 106, is used by XSL processor 118 (as more fully described below) to convert report_template.xml 104 from an XML file to an XSL stylesheet. The file 106 is employed to take the template information stored in report_template.xml 104 and create a stylesheet that may be applied to the report data contained in report_data.xml 102.

The stylesheet that is created by applying template_converter.xsl 106 to report_template.xml 104 is report_template.xsl 108. This resulting stylesheet 108 is applied to the report data contained in report_data.xml 102 using XSL processor 120 (as more fully described below) to produce a first intermediate file, formatted_report.xml 110. This first intermediate file 110 contains the original data to be published and information on how it is to be formatted, but not in terms of Extensible Stylesheet Language Formatting Objects (XSL-FO), which is the industry standard.

A third stylesheet, report_renderer.xsl 112, is applied to formatted_report.xml 110 using XSL processor 122 (as more fully described below) to transform the document into the standard XSL-FO markup. A second intermediate file, report.fo 114, is created that contains the data and how it should be formatted. Report.fo 114 is the final intermediate file, which is provided to a rendering engine to produce a formatted report. The formatted report may be a PDF (Portable Document Format) document, as shown by report.pdf 116. An alternative type of document, such as a Word document or HTML (Hypertext Markup Language) document, may be used for the formatted report. All such variations and any combination thereof are within the scope of the present invention.

The system 100 also employs XSL processors known in the art, such as SAXON, for applying the stylesheets to the input and intermediate XML files. XSL processor 118 applies template_converter.xsl 106 to report_template.xml 104 to produce report_template.xsl 108. XSL processor 120 applies report_template.xsl 108 to report_data.xml 102 to produce formatted_report.xml 110. XSL processor 122 applies report_renderer.xsl 112 to formatted_report.xml 110 to produce report.fo 114. In addition, the system 100 includes rendering engine 124 to render the formatted report (e.g. report.pdf 116) from the final intermediate file (e.g., report.fo 114).

Figure 2:
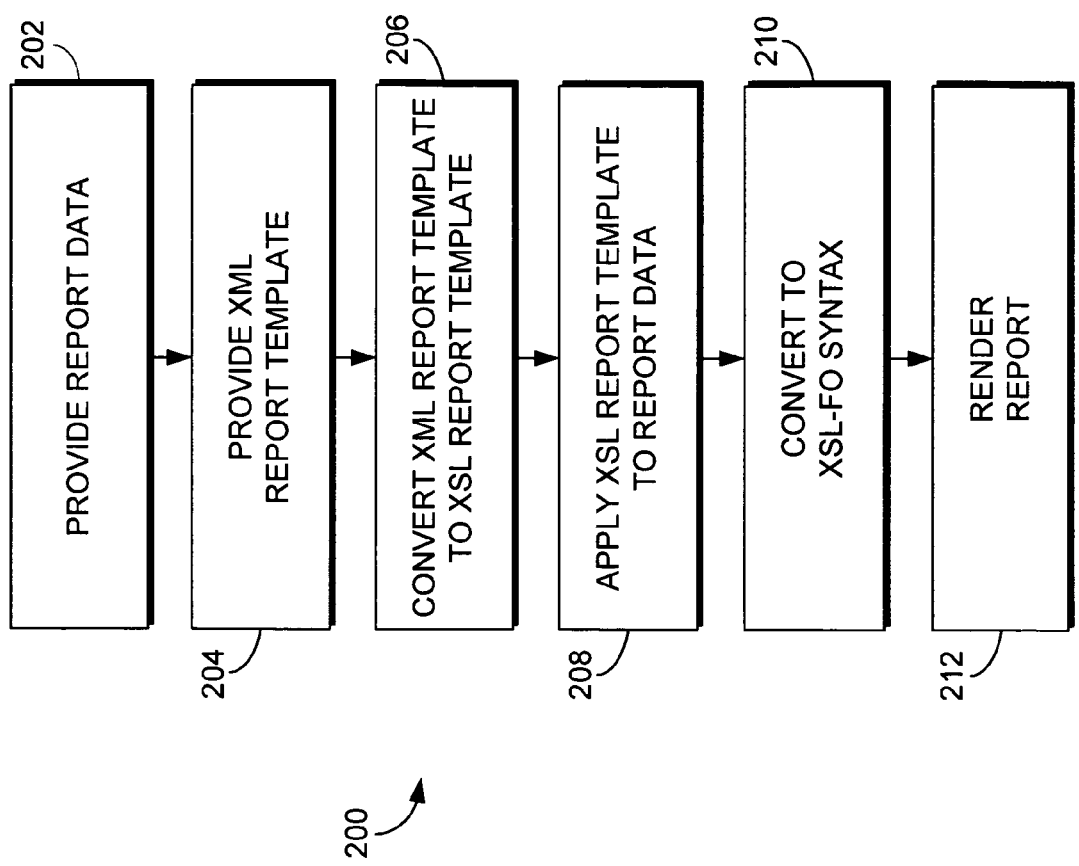
FIG. 2 is a flow diagram of a method for rendering a report in accordance with an embodiment of the present invention.

With reference to FIG. 2, a flow diagram of a method 200 for rendering a report in accordance with an embodiment of the present invention is illustrated. Initially, the system provides report data contained in an XML document, such as report_data.xml 102, as indicated at block 202. By way of example only and not limitation, in one embodiment, the XML data document may be generated by retrieving discrete data from a data base and converting the returned data into an XML representation using standard technologies such as Java Architecture for XML Binding (JAXB). Another exemplary embodiment would include retrieving the XML file directly from a file system. Next, as indicated at block 204, the system provides an XML report template, such as report_template.xml 104. The XML report template includes information regarding what data is to be included in the report and how the report should be formatted. The XML report template may be generated by writing an XML file with the required information. The method may also employ separate XML files that contain information regarding different components of the report template, and these separate template components may be combined into a single report template file. All such variations and any combination thereof are within the scope of the present invention.

Figure 3:
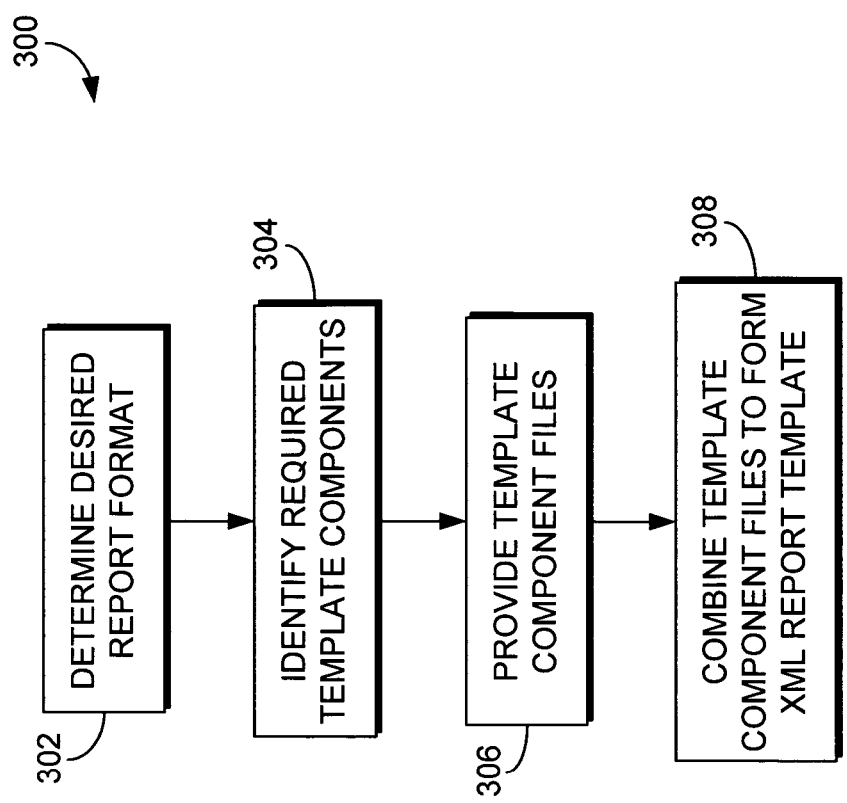
FIG. 3 is a flow diagram of a method for generating an XML report template in accordance with an embodiment of the present invention.

The latter approach to generating an XML report template is depicted by the flow diagram of FIG. 3, which illustrates an exemplary method 300 for building an XML report template using multiple template components. Initially, as indicated at block 302, the report format is determined. This step comprises determining what information is desired to be included in the rendered report and how the information should be presented.

Next, the template components required to build the template are identified, as indicated at block 304. The required template components include those components necessary to build a template capable of rendering a report with the desired format and content as determined in the step indicated at block 302. By way of example and not limitation, the available template components may include header components, footers components, and various section components.

After identifying the necessary template components, the file for each identified component is provided, as shown at block 306. Each file may consist of an XML document containing instructions regarding the format of a particular report section. Next, the various template components that were retrieved are combined to form an XML report template, as indicated at block 308.

Figure 4:
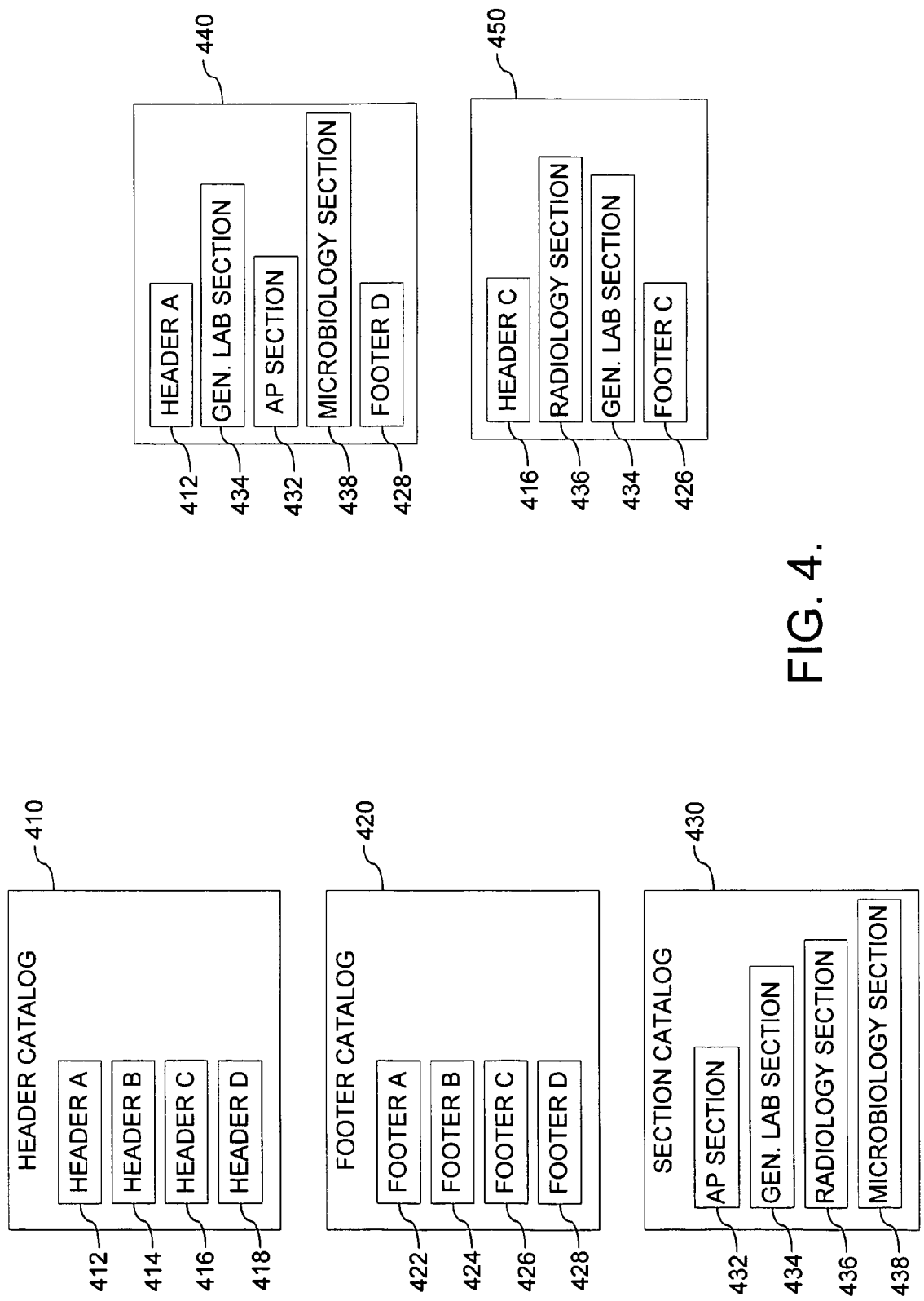
FIG. 4 is a schematic diagram illustrating template components and XML report templates generated using the template components in accordance with an embodiment of the present invention.

An exemplary depiction of template components and template builds for healthcare-related documents is illustrated in FIG. 4. Each template component includes an XML file containing instructions for a particular report section. The template components may be grouped into various component catalogs. For instance, FIG. 4 illustrates, by way of example only, a header catalog 410, a footer catalog 420, and a section catalog 430. Although only three component catalogs are shown in FIG. 4, it is contemplated within the scope of the invention that any number of component catalogs may be available.

The header catalog 410 contains a number of available header template components including Header A 412, Header B 414, Header C 416, and Header D 418. For healthcare-related documents, the header component may provide the ability to present information including, but not limited to, patient name, medical provider name, medical facility name, and the time period of treatment. Likewise, footer catalog 420 contains a number of available footer template components including Footer A 422, Footer B 424, Footer C 426, and Footer D 428. The footer components may provide the ability to present information including, but not limited to, page numbers and the date the report was rendered.

The section catalog 430 contains report sections that are available for the XML report template. Section catalog 430 illustrates a number of available sections including, but not limited to, an Anatomic Pathology (AP) Section 432, a General Lab Section 434, a Radiology Section 436, and a Microbiology Section 438. These section components provide the ability to pull and format data, such as medical testing results, for inclusion in the rendered report. Although each catalog 410, 420, 430 shows only four available template components, it is contemplated within the scope of the invention that any number of template components may be available for a template build.

FIG. 4 also illustrates two exemplary XML report templates built from the template components discussed above. The first exemplary report template 440 includes Header A 412, General Lab Section 434, AP Section 432, Microbiology Section 438, and Footer D 428. The second exemplary report template 450 includes Header C 416, Radiology Section 436, General Lab Section 434, and Footer C 426. As described above with reference to method 300, the report templates 440 and 450 may be built by determining the desired report format, identifying the necessary template components, retrieving the template component files, and combining the retrieved files into a single XML report template file.

Referring back to the method 200 of FIG. 2, once an XML report template has been provided, the XML report template is converted from an XML file to an XSL stylesheet, as shown at block 206. This is accomplished by applying a template converter stylesheet, such as template_converter.xsl 106, to the XML report template. Accordingly, an XSL report template, such as report_template.xsl 108, is created from the XML report template.

The XSL report template is applied to the report data, as shown at block 208, to generate an XML formatted report, such as formatted_report.xml 110. By applying the XSL report template to the report data, the formatting characteristics that were declared in the XML report template are merged with the report data. A number of functions are performed in this step. First, the XSL report template is used to explode out the report data into the appropriate report sections by data type. Second, the XSL report template is used to populate each of the chosen data elements and section parameters with the appropriate values from the report data. A third optional function is that the XSL report template is used to reorganize the report data for a section in a way that prepares it for further processing. The third function may only be necessary for complicated sections, such as where data flows along both X and Y axes.

Next, as shown at block 210, the XML formatted report is converted to XSL-FO syntax. This step is accomplished by applying a report renderer file, such as report_renderer.xsl 112, to the XML formatted report. The report renderer file is used to convert the syntax of the XML formatted report to XSL-FO syntax and apply the formatted rules of each section to the data. In addition, some sections may have table-wrapping logic, where columns that do not fit on a page carry down and start a new table below the current table.

Subsequently, the XSL-FO formatted report is rendered, as indicated at block 212. The XML-FO file is provided to a rendering engine, which produces the formatted report. As discussed previously, the formatted report may be any type of document known to those of ordinary skill in the art including, by way of example only, a PDF document, a Word document, or an HTML document.

With continuing reference to FIG. 2, as well as FIG. 5 though FIG. 12, an exemplary operation of the present invention is now described. FIG. 5 through FIG. 12 are exemplary input files, stylesheets, and intermediary files for rendering a report. In addition, FIG. 13 illustrates an exemplary PDF document, which may be rendered using the files and stylesheets of FIG. 5 through FIG. 12. The figures provide a simplified depiction of rendering a medical record according to an embodiment of the present invention. The present invention is not limited to strictly using the XML mark-up tags shown within these figures.

A patient, Sean P. Charting, upon being treated at a healthcare facility, has blood samples taken by a medical provider, who then sends the samples to a laboratory to determine a Creatinine level and a Chloride level. The laboratory technician inputs the medical test result information in a remote computer in the laboratory. For example, the technician may enter information, such as patient information, medical facility information, the date and time the samples were collected, and the results. In this example, samples were collected on Jan. 9, 2003 at 10:00, Jan. 10, 2003 at 14:30, and Jan. 13, 2003 at 8:14. The results were Creatinine levels of 001 mg/dL, 005 mg/dL, and 007 mg/dL, respectively, and Chloride levels of 102.3 mEq/L, 102.2 mEq/L, and 100.9 mEq/L, respectively. The data may be maintained in an XML data file to allow the current system to use the file to render a report, or as previously discussed, the file can be generated from the discrete data retrieved from a data base.

Subsequently, the system retrieves the XML data file, as indicated at block 202. An exemplary XML data file 500 retrieved by the step, as indicated by block 202, is depicted in FIG. 5. The file 500 comprises an XML document containing information that is to be presented in the report. As shown in FIG. 5, the file 500 contains demographic data, such as patient information, including the patient's name, "Sean P. Charting," the patient's gender, "Male," the patient's date of birth, "Jul. 31, 1978," and the patient's social security number, "111-22-3333." The file 500 contains additional demographic data regarding the treating facility, including the facility name, "Baseline East Medical Center," the facility designation, "BEMC," and the date and time of admittance at the facility, "Jan. 8, 2003 11:16." The file 500 also contains clinical data, which represents the laboratory testing results. The data includes the date and time when samples were collected, the parameter that was tested, and the results. For example, the file 500 indicates that the sample designated accession number 03-134-56 was collected on Jan. 9, 2003 at 10:00 and the results for Creatinine were 001 mg/dL.

Figure 6:
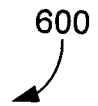
FIG. 6 is an exemplary XML report template file in accordance with an embodiment of the present invention.

Next, as indicated at block 204, the system retrieves an XML report template, such as the exemplary XML report template 600 depicted in FIG. 6. As discussed previously, the XML report template 600 contains information regarding what data is to be extracted and presented in the report and how the report should be formatted. The file 600 may have been generated by writing the code for the file or by retrieving and combining various template components. As shown in FIG. 6, the exemplary XML report template 600 includes a header section, a body section, and a footer section.

Subsequently, as indicated at block 206, a template converter stylesheet is applied to the XML report template 600 to convert the file to an XSL report template. An exemplary template converter stylesheet 700 is shown in FIG. 7A-7C. The converter stylesheet 700 contains the necessary instructions to convert the XML report template into an XSL report template. FIG. 8A-8B illustrate the template stylesheet 800 created by applying the template converter stylesheet 700 to the XML report template 600.

After the template stylesheet 800 has been created, it may be applied to the XML data file 500, as indicated at block 208. FIG. 9 illustrates an exemplary resulting XML formatted report 900. The report 900 contains both the data to be presented in the rendered report, as well as information regarding how the data is to be formatted.

Next, as indicated at block 210, a report renderer stylesheet is applied to the XML formatted report 900. An exemplary report renderer file 1000 is illustrated in FIG. 10A-10B. The report renderer file 1000 provides further processing as described above to convert the XML formatted report 900 to the standard XSL-FO format. The report renderer 1000 includes a reference to an additional file, "sect_vertical_lab.xsl," which is depicted in FIG. 11A-11B as file 1100 and sets forth parameters for a vertical laboratory section. As demonstrated by the reference to this file, different section types can be modeled using separate XSL stylesheets that are imported by the report renderer file. The XSL-FO formatted report 1200 that is generated by applying the report renderer file 1000 to the XML formatted report 900 is depicted in FIG. 12A-12C. This file contains the data to be presented and formatting information in the standard XSL-FO format.

As indicated at block 212, a final report may be rendered from the XSL-FO formatted report 1200. For example, FIG. 13 illustrates the rendered report as a PDF document 1300. The report 1300 includes the desired data originating from the XML data file 500 presented in the format contained in the XML report template 600. The report 1300 may be maintained with Sean Charting's records and provided to the treating physician for diagnostic and treatment purposes, or the like.

The present invention has been described in relation to particular embodiments, which are intended in all respects to be illustrative rather than restrictive. Alternative embodiments will become apparent to those of ordinary skill in the art to which the present invention pertains without departing from its scope. Substitutions may be made and equivalents employed herein without departing from the scope of the invention as recited in the claims. For example, additional steps may be added and steps omitted without departing from the scope of the invention. It will be understood that certain features and subcombinations are of utility and may be employed without reference to other features and subcombinations. This is contemplated by and is within the scope of the claims.

The invention claimed is:

1. A method in a computer system for dynamically rendering a report in a healthcare environment, the method comprising:
   receiving an XML file including a set of medical results of a patient and a patient name, wherein the set of medical results and the patient name is to be presented in the report;
   providing a plurality of section templates, wherein each section template in the plurality of section templates includes a respective XML template file that defines a respective format of a respective section;
   receiving a selection of a section template from among the plurality of section templates, wherein the section template provides an XML template file that defines a format of a section, which categorizes the set of medical results of the patient;
   converting the XML template file to an XSL stylesheet, which defines the format of the section and a header format;
   applying the XSL stylesheet to the set of medical results of the patient contained in the XML file to create a formatted XML file, wherein the formatted XML file contains the set of medical results to be presented in the report and data representing the header format for the report; and
   rendering the report using the formatted XML file, wherein the set of medical results are rendered according to the format of the section and the patient name is rendered according to the header format.

2. The method of claim 1, wherein the section template is combined with other templates when creating the XML template file.

3. The method of claim 2, wherein the other templates include a header template and a footer template.

4. The method of claim 1, wherein converting the XML template file to the XSL stylesheet comprises applying an intermediary XSL stylesheet to the XML template file.

5. The method of claim 1, wherein rendering the report using the formatted XML file comprises:
   converting the formatted XML file to an XSL-FO file; and
   rendering the report from the XSL-FO file.

6. The method of claim 5, wherein converting the formatted XML file to the XSL-FO file comprises applying an intermediary XSL stylesheet to the formatted XML file.

7. The method of claim 1, wherein the set of medical results includes medical-test results.

8. The method of claim 1, wherein the report comprises a medical record.

9. The method of claim 1, wherein the report comprises a PDF document, a Word document, or an HTML document.

10. Computer-storage media having computer-usable instructions, that when executed by a computing device, perform a method for dynamically rendering a report in a healthcare environment, the method comprising:
   receiving an XML file including diagnostic-test results of a patient and a patient name, wherein the diagnostic-test results and the patient name are to be presented in the report;
   providing a plurality of section templates, wherein each section template in the plurality of section templates includes a respective XML template file that defines a respective format of a respective section;
   receiving a selection of a section template from among the plurality of section templates, wherein the section template provides an XML template file that defines a format of a section, which categorizes the diagnostic-test results of the patient;
   converting the XML template file to an XSL stylesheet, which defines the format of the section and a header format;
   applying the XSL stylesheet to the diagnostic-test results in the XML file to create a formatted-XML file, wherein the formatted XML file contains the diagnostic-test results to be presented in the report and data representing a header format for the report; and rendering the report using the formatted XML file, wherein the diagnostic-test results are rendered according to the format of the section and the patient name is rendered according to the header format.

11. The media of claim 10, wherein the section includes a general-lab section, an anatomic pathology section, a radiology section, or a microbiology section.

12. A system that comprises a processor and a computer-storage medium and that leverages the processor to execute computer-executable instructions, which are stored on the computer-storage medium and provide a method of rendering a report in a healthcare environment, the method comprising:

receiving an XML file including diagnostic-test results of a patient and a patient name, wherein the diagnostic-test results and the patient name are to be presented in the report;

providing a plurality of section templates, wherein each section template in the plurality of section templates includes a respective XML template file that defines a respective format of a respective section;

receiving a selection of a section template from among the plurality of section templates, wherein the section template provides an XML template file that defines a format of a section, which categorizes the diagnostic-test results of the patient;

converting the XML template file to an XSL stylesheet, which defines the format of the section and a header format;

applying the XSL stylesheet to the diagnostic-test results in the XML file to create a formatted XML file, wherein the formatted XML file contains the diagnostic-test results to be presented in the report and data representing the header format for the report; and rendering the report using the formatted XML file, wherein the diagnostic-test results are rendered according to the format of the section and the patient name is rendered according to the header format.

13. The media of claim 12, wherein the section includes a general-lab section, an anatomic pathology section, a radiology section, or a microbiology section.

* * * * *